United States Patent

Ryan

Patent Number: 5,727,552
Date of Patent: Mar. 17, 1998

[54] CATHETER AND ELECTRICAL LEAD LOCATION SYSTEM

[75] Inventor: Terence G. Ryan, Palm Coast, Fla.

[73] Assignee: Medtronic, Inc., Minneapolis, Minn.

[21] Appl. No.: 584,872

[22] Filed: Jan. 11, 1996

[51] Int. Cl.[6] .................................................... A61B 5/00
[52] U.S. Cl. ................................. 128/653.1; 128/899
[58] Field of Search ........................... 128/653.1, 642, 128/899

[56] References Cited

U.S. PATENT DOCUMENTS

| | | |
|---|---|---|
| 4,154,246 | 5/1979 | LeVeen . |
| 4,697,595 | 10/1987 | Breyer . |
| 5,078,678 | 1/1992 | Katims . |
| 5,099,845 | 3/1992 | Besz et al. ................. 128/653.1 |
| 5,201,865 | 4/1993 | Kuehn . |
| 5,211,165 | 5/1993 | Dumoulin et al. ............ 128/653.1 |
| 5,231,996 | 8/1993 | Bardy . |
| 5,312,446 | 5/1994 | Holschbach . |
| 5,374,286 | 12/1994 | Morris . |
| 5,443,489 | 8/1995 | Ben-Haim . |
| 5,445,150 | 8/1995 | Dumoulin et al. ............ 128/653.1 |

*Primary Examiner*—Scott M. Getzon
*Attorney, Agent, or Firm*—Reed A. Duthler; Harold R. Patton

[57] ABSTRACT

A system for precisely locating the distal end of a catheter or an electrical stimulation and/or sensing lead, particularly a pacing lead or a defibrillation lead, within a patient's body. In a first embodiment employing a passive LC resonant circuit having a resonant oscillating frequency incorporated into a catheter or lead distal tip which may be located by means for and the steps of generating a field outside the patient's body at the resonant oscillating frequency encompassing the patient's body and the implanted catheter for a predetermined time to cause the resonant circuit to store energy and oscillate, terminating the generated field, whereby the resonant circuit continues to oscillate as the stored energy is dissipated and creates a re-radiated magnetic field, detecting the re-radiated magnetic field, and determining the location of the catheter distal tip as a function of the detected re-radiated magnetic field. In a further embodiment involving an active LC resonant circuit in a lead coupled to an implanted pulse generator having a source of electrical energy, the active resonant circuit may be selectively energized to oscillate at a resonant frequency and radiate a magnetic field in response to an energizing signal applied through the electrical conductor. The location of the catheter distal tip is identified as a function of the radiated magnetic field as detected and measured outside the patient's body.

10 Claims, 5 Drawing Sheets

5,727,552

CATHETER AND ELECTRICAL LEAD LOCATION SYSTEM

FIELD OF THE INVENTION

The present invention relates to a system for precisely locating the distal end of a catheter or an electrical stimulation and/or sensing lead, particularly a pacing lead or a defibrillation lead, within a patient's body.

DESCRIPTION OF THE BACKGROUND ART

For a wide range of medical reasons, medical catheters and electrical sensing and/or stimulation electrode bearing leads are introduced into a patient's body either temporarily or chronically for monitoring and/or therapeutic operations. In many of the medical applications for these devices, it is necessary to precisely locate a structure at or near the distal end of the catheter or lead body in relation to specific body tissue in a body cavity or vessel.

For example, endocardial pacing electrode bearing leads and cardioversion/defibrillation electrode bearing leads may be transvenously introduced into a heart chamber or a blood vessel adjoining the heart and precisely positioned in relation to specific heart structure in order to sense electrical depolarizations of a heart chamber and to provide specific current pathways for applied pacing pulses or cardioversion/defibrillation shocks. In a further medical procedure, cardiac mapping catheters are introduced into a heart chamber to make measurements of cardiac depolarization signals at precisely located conduction pathways of the heart. Cardiac ablation catheters are similarly positioned to apply ablation energy to a conduction pathway in order to eradicate it. Other electrical sensing and stimulation leads are implanted in spinal cord stimulation systems in relation to a specific spinal cord location. In all of these cases, there is a possibility that the sensing or stimulation or ablation electrodes may not be properly positioned with respect to the specific body structure or tissue. Positioning is typically monitored employing fluoroscopy to image a radiopaque member at the distal tip region of the lead and visually following the advancement in relation to body structure that is faintly outlined in the image.

Similarly, catheters of various types, including balloon catheters, infusion catheters, drainage catheters, or the like, are advanced through blood vessels to a site in a vessel or organ where monitoring or drug therapies or the like are delivered or effected. Typically catheters are provided with radiopaque bands or structures that can also be visualized under fluoroscopy. In addition, radiopaque fluids may also be introduced to visualize the location of the catheter tip and the adjacent blood vessel or organ lumen.

The positioning attained by fluoroscopic monitoring can be imprecise, depending in part on the degree of difficulty in reaching or identifying the body structure that is sought to be accessed. Moreover, repeated and prolonged exposure to the imaging rays can be harmful to the attending staff.

Consequently, efforts have been undertaken to develop methods and apparatus for locating catheter tips employing other means for visualizing the catheter tips. A first approach involving echocardiography as described, for example, in U.S. Pat. No. 4,697,595. A catheter tip is formed having a plurality of ultrasonic piezoelectric elements coupled to lead pairs extending proximally outside the patient to a signal processor for processing the output signals generated by the elements in response to an applied ultrasonic transducer probe.

In mapping active arrhythmic sites or conduction pathways of the heart, the intrinsic depolarizations of heart tissue can be tracked to locate the catheter tip with respect to specific cardiac tissue as also described in U.S. Pat. No. 5,078,678.

Also in the context of mapping cardiac tissue conduction pathways for ablation, it has been proposed to incorporate a transmitter antenna or receiver antenna in the mapping and ablation tip electrode in U.S. Pat. No. 5,443,489. Radio frequency (rF) wave signals are transmitted between the catheter transmitter or receiver antenna and an external, three dimensional, receiver antenna array or transmitter antenna array, respectively. The rF signals are either transmitted to or received from the catheter antenna by separate catheter conductors from catheter conductors coupled to the mapping or ablation electrodes. In most miniature catheters and leads, it is undesirable to unduly multiply the number of lead conductors which can lead to enlargement of the lead diameter and can decrease the ability to advance it into vessel lumens or chambers of small size.

The implantation of endocardial pacing leads and defibrillation leads is typically conducted under fluoroscopy to position distal tip pace/sense electrodes in the right atrial appendage or the right ventricular apex or, less frequently, in other suitable locations. Typically, the amplitude of the intrinsic heart depolarization signal is measured during implantation, and the tip electrode is re-positioned to an optimal signal strength position. Such leads are typically provided with distal tip active or passive fixation mechanisms for attachment to or engagement against heart tissue once the optimum position is attained in order to inhibit movement of the distal tip and migration of the lead into another heart chamber or a blood vessel. Nevertheless, from time to time, dislodgement may occur, and the abilities to sense cardiac depolarizations and to pace and capture the heart may be lost. Physicians then have to intervene to locate and re-position the lead, if possible.

SUMMARY OF THE INVENTION

It is accordingly an object of the present invention to provide a catheter or lead distal tip location system that does not require additional conductors to transmit power to or receive signals from the distal tip.

It is a further object of the present invention to provide a passive catheter or lead distal tip location system requiring no power source or conductors to transmit power to or receive signals from the distal tip.

Hereinafter, and particularly in the claims following the detailed description, a "catheter" is intended to include a "lead" of the types described above for conducting electrical signals to and from the body unless either one is otherwise particularly specified. Stated another way, a lead is a type of catheter having one or more electrical conductors used to conduct sensed electrical signals, typically intrinsic electrical signals of a body organ, or to conduct electrical energy to a body organ.

These and other objects of the invention are realized in a first embodiment employing a passive resonant circuit having a resonant oscillating frequency incorporated into a catheter distal tip which may be located by means for and the steps of generating a magnetic field outside the patient's body at the resonant oscillating frequency encompassing the patient's body and the implanted catheter for a predetermined time to cause the resonant circuit to store energy and oscillate, terminating the generated field, whereby the resonant circuit continues to oscillate as the stored energy is dissipated, detecting the continued oscillation of the resonant circuit from re-radiated magnetic fields, and determining the location of the catheter distal tip as a function of the re-radiated magnetic field. The passive resonant circuit is preferably an LC tank or ringing circuit incorporated into the tip structure of any catheter, and is particularly of use in a pacing lead, defibrillation lead or other electrical sensing or stimulation lead.

These and other objects of the invention are also realized in a second embodiment particularly useful with a stimulation or sensing lead having an electrical conductor extending to each respective exposed electrode of the lead employing an active resonant circuit having a resonant oscillating frequency incorporated into the distal tip structure and electrically connected to the electrical conductor. In this embodiment, the active resonant circuit may be selectively energized to oscillate at a resonant frequency in response to an energizing signal applied through the electrical conductor. The location of the catheter distal tip is identified as a function of the radiated field as detected by a receiving antenna array developing signals that are measured and compared.

In particular, the active resonant circuit is preferably an LC circuit that bridges a pair of electrical conductors in a bipolar lead or that extends from the single electrical conductor of a unipolar lead and the effective ground of the patient's body through a further exposed auxiliary conductive surface, which may be one of the capacitor plates.

The active resonant circuit embodiments may be implemented in conjunction with a resonant frequency signal generating circuit incorporated into chronically implantable monitors or implantable pulse generators of pacemakers, cardioverter/defibrillators or other stimulators that are remotely programmable from outside the patient's body by a physician using a programmer. The energization of the active resonant circuit(s) to locate the lead tip(s) by the resonant frequency signal generating circuit may be initiated by a programmed-in command in order to minimize energy consumption. The energizing signals are of a frequency and amplitude that do not elicit a body tissue response or otherwise affect the operations of the implantable monitor or pulse generator, including the pulse waveform emitted by a pulse generator. In this embodiment, the detection and measurement may be conducted during the delivery of the energizing signal since the external receiver is independent of the resonant frequency signal generating circuit.

Alternatively, as in the first embodiment, upon terminating the energizing signal, the resonant circuit continues to oscillate as the stored energy is dissipated. The continued oscillation of the resonant circuit generates a re-radiated magnetic field, and it may be detected and the catheter tip location determined from it during the continued oscillation.

In systems involving more than one such catheter or lead, e.g. a permanently implanted dual chamber pacing system with leads bearing atrial and ventricular pace/sense electrodes, the resonant frequencies for the LC resonant circuits of the atrial and ventricular leads preferably differ from one another so that LC resonant circuits store energy and oscillate only at their frequencies.

The practice of the invention therefore requires no electrical conductors in catheters not already having electrical conductors nor or any additional conductors than those already present in leads of the type described.

BRIEF DESCRIPTION OF THE DRAWINGS

Other objects, advantages and features of the present invention will become apparent from the following specification when taken in conjunction with the accompanying drawings in which like elements are commonly enumerated and in which.

DESCRIPTION OF THE PREFERRED EMBODIMENTS

Turning now to the first embodiment of the invention, the passive approach utilizes a physically small, resonant circuit 10 comprising an inductor L and a capacitor C electrically connected together in a tank circuit configuration and built into the catheter near the distal tip. The LC resonant circuit 10 shown in FIG. 1 has a self resonant frequency as a function of the inductance and capacitance of the inductor L and capacitor C as is well known in the art. In the illustration of the principles of the first embodiment depicted in FIGS. 1–4, the catheter is a lead 12, which may be a pace/sense lead or a monitoring lead, and the LC resonant circuit 10 is not electrically connected to any conductor in the lead body and hence does not affect the sensing, stimulation or other system performance in any way.

Figure 1:
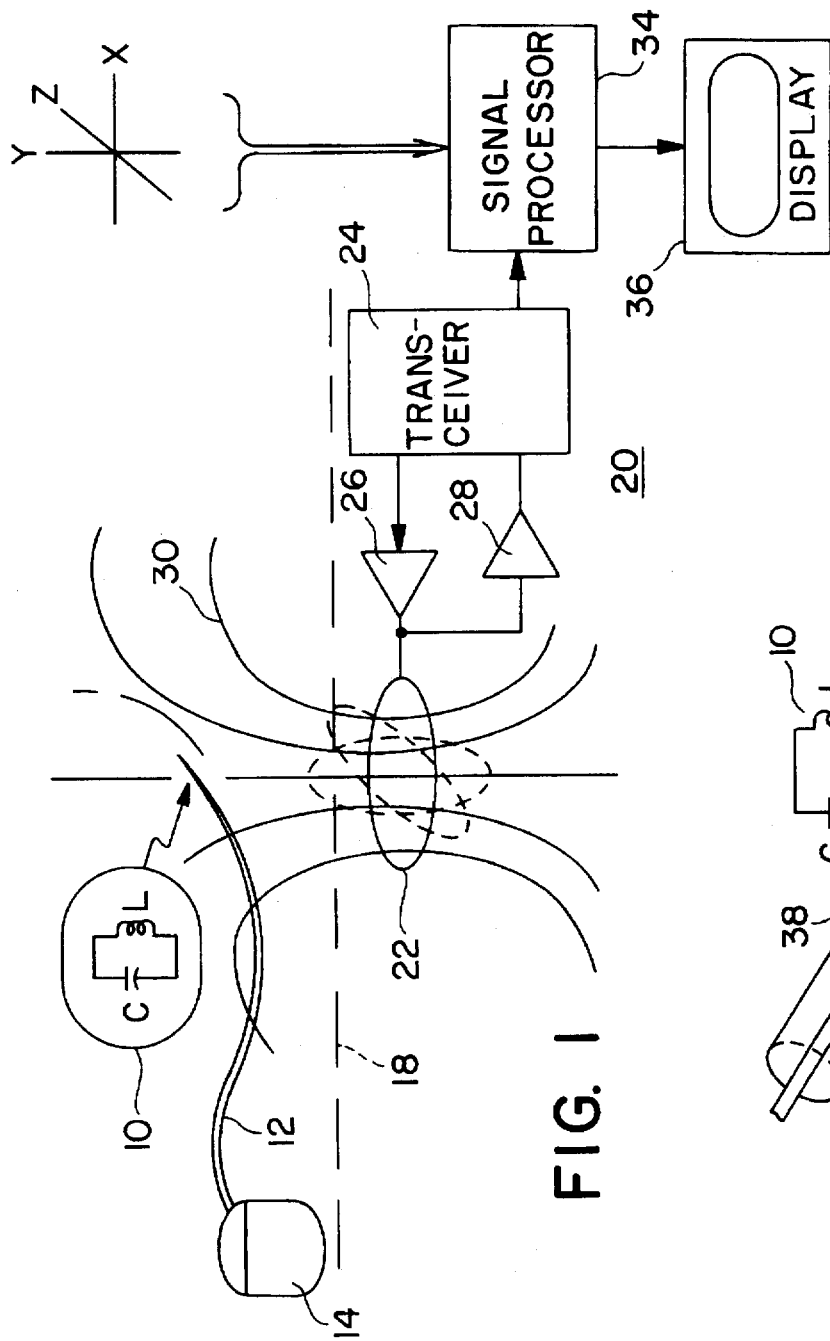
FIG. 1 is a schematic illustration of the external transmission of energy through at least one antenna loop of an antenna array to an implanted, passive, LC resonant circuit at the distal tip of a catheter by a location system in accordance with a first embodiment of the invention.
Figure 2A:
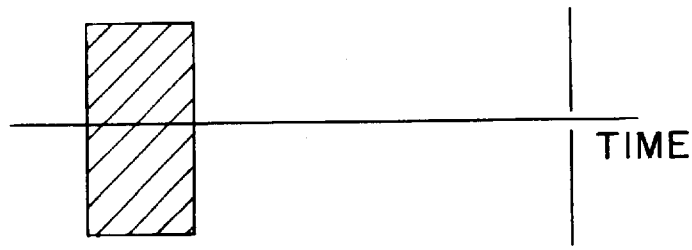
FIGS. 2A–2C are illustrations of the transmitted signal, the responsive ringing of the LC resonant circuit, and the re-radiated signal waveform detected by the location system in accordance with the first embodiment of the invention.
Figure 2B:
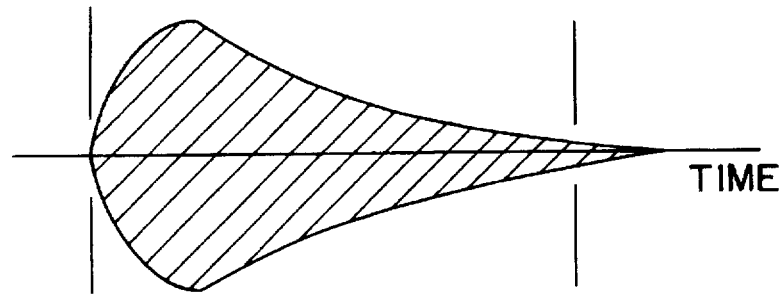
Figure 3:
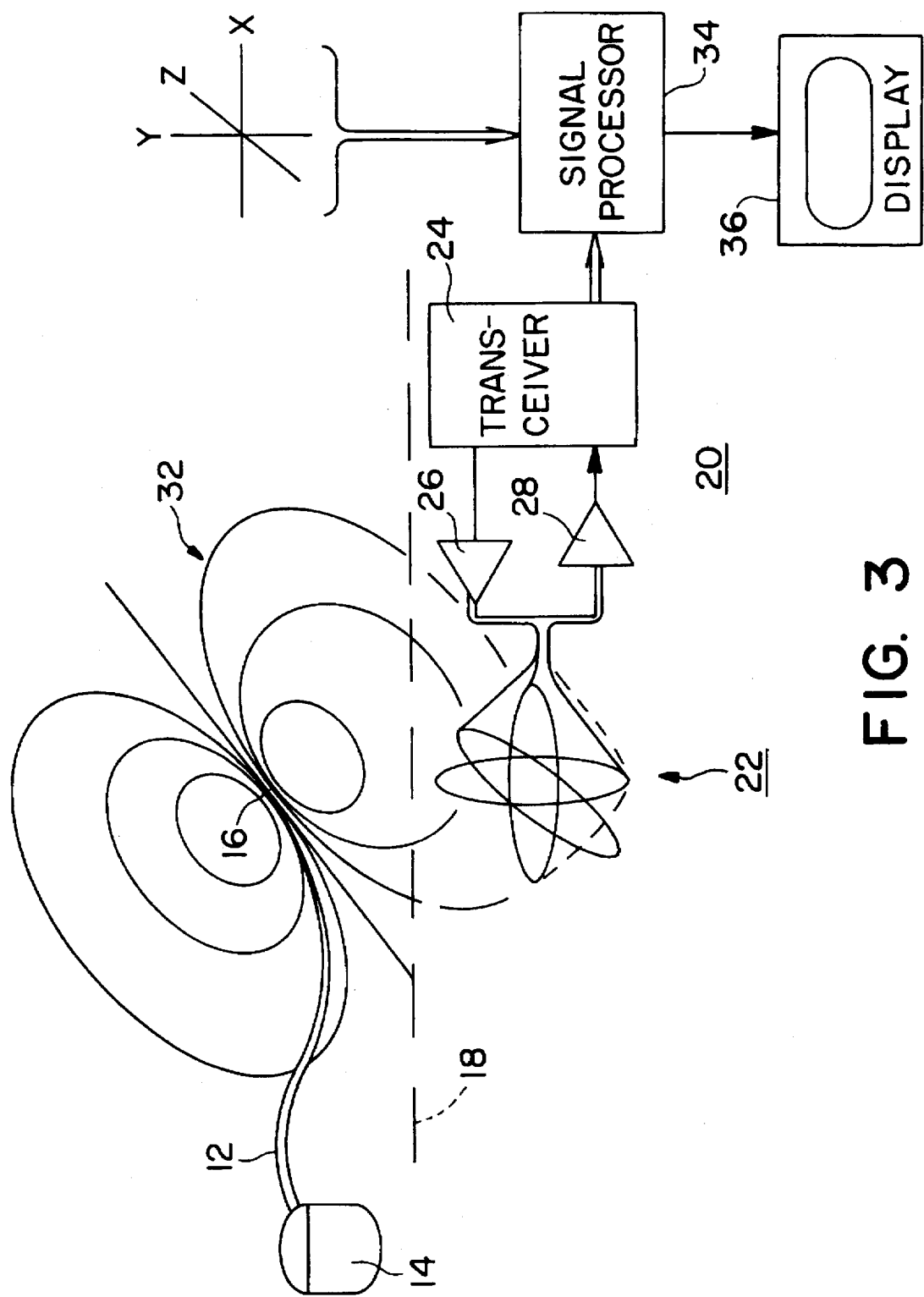
FIG. 3 is a schematic illustration of the re-radiation of energy from the implanted, passive, LC resonant circuit at the distal tip of the catheter by the location system operating in a receive mode in accordance with the first embodiment of the invention.

As shown in FIGS. 1 and 3, the lead 12 is attached at its proximal end to an implantable pulse generator (IPG) 14 or a monitor of any of the known types. In this illustration, it will be understood that the LC resonant circuit 10 is in the pacing lead tip 16 implanted within the patient's heart inside the patient's body and skin 18. The lead tip 16 location process is initiated when the physician positions a multiple loop antenna array 22 of a location system 20 outside the patient's skin 18. The antenna array 22 preferably includes three or more orthogonally disposed loops oriented in appropriate directions, of the type disclosed in the above-referenced '489 patent. The transceiver 24 is operated in a transmit mode to trigger transmitter oscillator and amplifier stage 26 to emit an rF pulse, shown in FIG. 2A, through at least one antenna loop of antenna array 22 at the self resonant frequency of the LC resonant circuit 10. Energy from this transmitted pulse of FIG. 2A is radiated as radiating field 30 depicted in FIG. 1 and inductively coupled into the LC resonant circuit 10 causing an oscillating current to build up at the LC resonant frequency as shown in FIG. 2B.

Figure 2C:
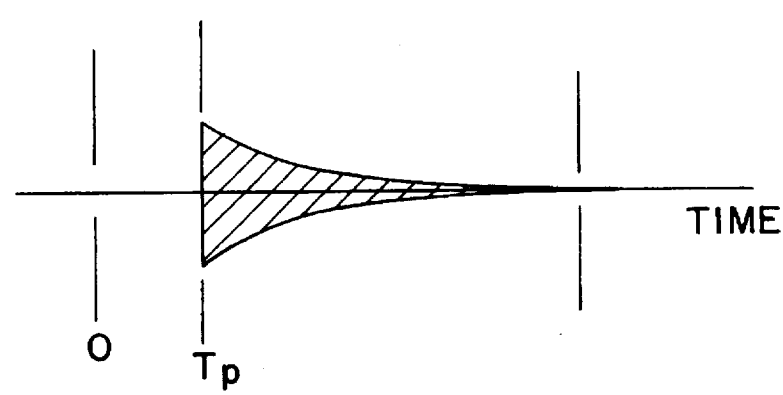

The transmitted pulse is then terminated at time $T_p$, and the transceiver 24 is switched to a receive mode. The LC resonant circuit 10 continues to oscillate or "ring" with a decaying time constant related to the Q of the LC circuit 10 as shown in FIG. 2B. The decaying, oscillating signal is re-radiated from the LC resonant circuit 10 as re-radiated field 32 depicted in FIG. 3. The re-radiated signal, shown in FIG. 2C, is picked up by the locating system antenna array 22 which provides three (or more) signals of intensity related to the orientation of the antenna loops to the re-radiated field. The three (or more) signals are processed through receiver amplifier stage 28 and provided to transceiver 24 as shown in FIG. 3.

The signals received from the loops of the antenna array 22 contain sufficient information for system processing algorithms included in the signal processor 34 to determine the lead tip 16 location in the patient's body. The received signals are applied to the signal processor 34 which is referenced to a set of X, Y, Z reference plane coordinates related to the table the patient is reclining on. The spatial position of lead tip 16 is mathematically derived in a manner described in the above-referenced '489 patent and displayed on the display 36. The signal processor 34 and display 36 may be embodied in a personal computer.

Figure 4:
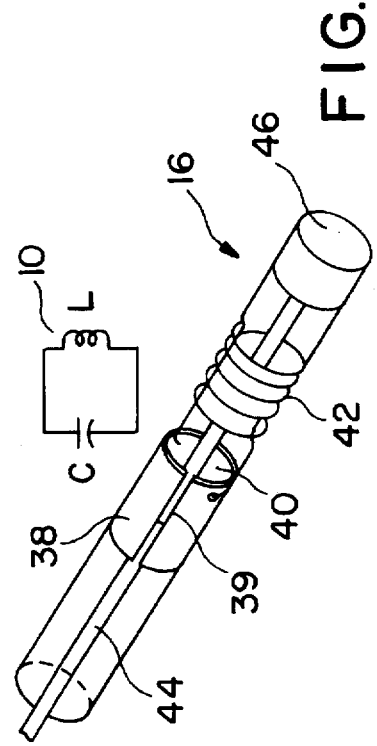
FIG. 4 is an enlarged perspective view of the components of the passive LC resonant circuit incorporated into the distal tip of a lead.

The LC resonant circuit 10 can be built into a pacing or cardioversion/defibrillation lead tip requiring little if any additional volume as shown by the expanded perspective illustration of FIG. 4. The LC resonant circuit 10 may, for example, be incorporated into the distal tip region of the endocardial pacing leads of the type disclosed in U.S. Pat. No. 5,231,996, incorporated herein by reference, within an additional outer insulation sleeve proximal to the fixation mechanism.

In FIG. 4, two coaxial, cylindrical capacitor plates 38 and 40 and an inductor coil 42 are shown mounted end to end within the outer insulating sheath (not shown) of the lead 12. The ends of the inductor coil 42 are electrically connected to the cylindrical capacitor plates 38 and 40.

The inner and outer cylindrical capacitor plates 38 and 40 have longitudinal breaks formed therein to prevent electrical shunting of the oscillating field of inductor coil 42. If space permits, the inductor coil 42 could be wound directly over the outer cylindrical capacitor plate 38 or inside the inner cylindrical capacitor plate 40, rather than the end-to-end arrangement depicted.

The conductor 44 is shown passing within these LC components to a tip electrode 46 and is electrically insulated therefrom by an inner sheath (not shown). The conductor 44 is electrically connected to a distal tip electrode 46 in a manner well known in the art. In bipolar lead configurations, the capacitor/inductor components may be located between a proximal ring electrode (not shown) and the combination of the distal tip electrode 46 and the fixation mechanism (not shown). It will be understood that any of the conventional active or passive fixation mechanisms may also be incorporated into the lead distal tip 16.

Depending on the system resonant frequency employed, resonance may be achieved using a single plate capacitor surrounding the windings of inductor coil or the self resonance of the inductor itself without a discrete capacitor. In order to ease manufacturing tolerances, the specified resonant frequency of any given LC resonant circuit 10 may be broadly toleranced and the actual resonant frequency may be determined in testing after assembly is completed. The location system 20 may be provided with an adjustable frequency oscillator and amplifier stage 26, and the resonant frequency, if unknown, may be determined by sweeping the frequency range and monitoring the response to detect the peak amplitude of the re-radiated field.

Figure 5:
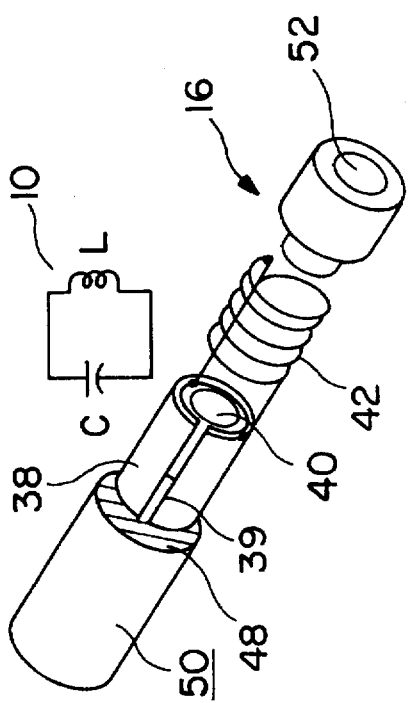
FIG. 5 is an enlarged perspective view of the components of the passive LC resonant circuit incorporated into the distal tip of a catheter.

Although the first, passive embodiment of the invention is illustrated in FIGS. 1-4 in the context of a cardiac pacemaker, it will be understood that the LC resonant circuit may be incorporated into the distal tip region of any other electrical sensing and/or stimulation lead for any monitor and/or stimulation system. Moreover, as explained above, the LC resonant circuit 10 may also be incorporated into a catheter, and the catheter tip may be located employing the same location system 20 as described above. For example, the LC resonant circuit 10 is illustrated in the expanded perspective illustration of FIG. 5 built into the side wall 48 of a hollow lumen catheter 50 near the distal tip end opening 52 thereof. The catheter 50 may take any of the forms well known in the art and may include further structure including balloons, side wall or end openings, valves in the openings, multiple lumens, sensors, etc, and used for in any of the wide applications presently practiced or contemplated. The inner and outer cylindrical capacitor plates 38 and 40 and the inductor coil 42 and the interconnections thereof to form the miniature passive LC resonant circuit 10 are interposed inside the wall or between inner and outer sheathes of the catheter 50 near the distal end thereof. The miniature passive LC resonant circuit 10 does not interact with any other structure of a catheter and affect the performance or operation thereof. The LC components may be fabricated of high radiopaque density materials, e.g. platinum, gold or the like and also function as radiopaque catheter tip markers in a manner well known in the art.

Turning to the second, active embodiment of the invention, it is preferably practiced in the context of a sensing and/or stimulation lead of the types described above already having one or more electrical conductor extending to a distal end or region thereof. However, rather than being coupled together in a tank circuit configuration, the inductor L and capacitor C are coupled in series since a parallel connection could result in effectively shorting the lead conductor or conductors through the inductor L at lower frequencies, including pacing pulse frequencies, for example. The inductor L and capacitor C are otherwise mechanically LC) formed in the lead body in the manner described above with respect to FIG. 4.

Figure 6:
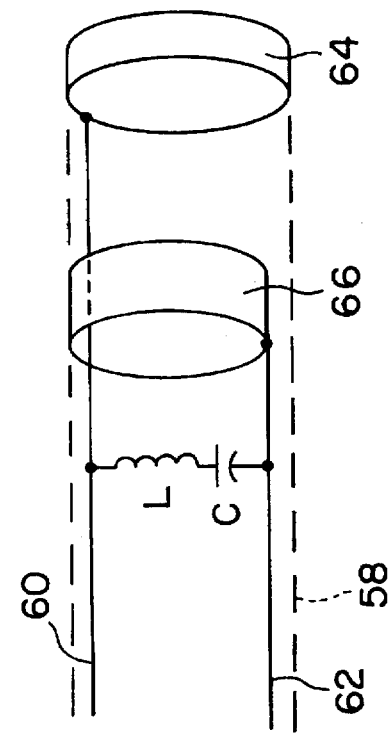
FIG. 6 is a schematic illustration of the active LC resonant circuit of the second embodiment of the invention coupled to bipolar lead conductors.

In a first variation of this active LC resonant circuit embodiment shown in FIG. 6, the series LC resonant circuit 10' is formed in a bipolar lead 58. The series LC resonant circuit 10' is electrically connected across the two electrical lead conductors 60 and 62 and thereby electrically connected between the tip electrode 64 and the ring electrode 66.

Figure 7:
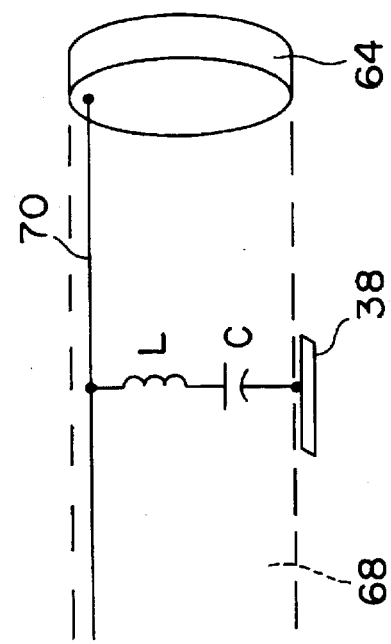
FIG. 7 is a schematic illustration of the active LC resonant circuit of the second embodiment of the invention coupled to unipolar lead conductors.

In the second variation of this active LC resonant circuit embodiment shown in FIG. 7, the series LC resonant circuit 10' is formed in a unipolar lead 68. In unipolar leads, the electrical return path is established through the body and by a further, exposed indifferent electrode, which typically is the exposed conductive case of the IPG or monitor or the like. The series LC resonant circuit 10' is electrically connected between the single electrical lead conductor 70, and thereby electrically connected to the tip electrode 64, and to a further electrode 72 at the surface of the lead body. The further electrode 72 may be formed by an exposed area of the outer cylindrical capacitor plate 38. In this manner, the return path for the energizing signal is through the patient's body and to the indifferent electrode.

In either variation, a very low amplitude energizing pulse signal at the LC resonant frequency (of the type shown in FIG. 2A) is directly fed to the LC resonant circuit '10 via the lead conductor(s). The LC resonant circuit '10 resonates as described above with reference to FIG. 2A, and the ringing current induced in the LC resonant circuit '10 creates a radiated field of the type shown in FIG. 2B that can be detected by the location system 20 operating in the receive mode as described above in reference to FIG. 3.

It should be noted that while FIG. 2A shows an energizing pulse of relatively short duration, the energizing signal may be longer. In this second, active mode, the radiated magnetic field signal of the type shown in FIG. 2B may be detected during the delivery of the energizing pulse of the type shown in FIG. 2A, since the energizing signal is not transmitted by the antenna array 22. The energizing signal of the type shown in FIG. 2A may be applied continuously for as long as it takes to detect and measure of the radiated signal and to determine the lead tip location. It is preferred that the energizing pulse 2A be as short as possible to avoid unnecessary depletion of the implanted device battery or interference with the device operation.

This active approach does not place a DC path across the lead conductors and presents a very high impedance to physiologic signals. The low amplitude rF signal required for this approach is far removed from the physiologic spectrum and has no effect on normal pacing operations. Moreover, it need not consume undue amounts of battery energy.

Figure 8:
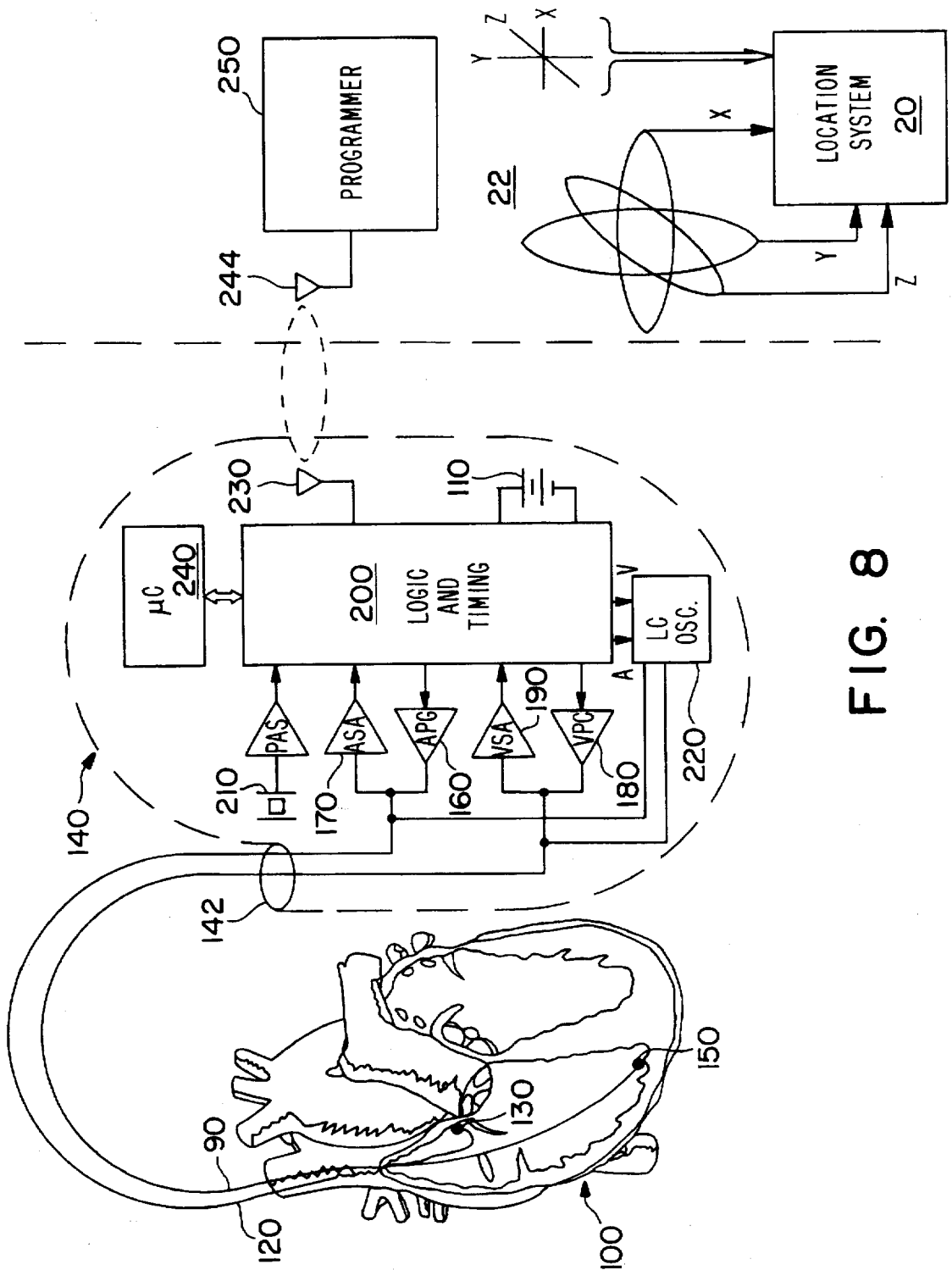
FIG. 8 is a schematic illustration of a second embodiment of the location system of the present invention for locating distal tips of leads.

Turning to FIG. 8, it illustrates how the second embodiment may be practiced in the context of the pace/sense functions and components of a dual chamber, multi-programmable pacemaker (or pacemaker/cardioverter/ defibrillator) of any of the types known in the art. The pace/sense IPG 140 is provided with a hermetically sealed enclosure, typically fabricated of biocompatible metal such as titanium. Mounted to the top of the enclosure is a connector block assembly 142, which receives electrical connectors located on the proximal ends of atrial lead 120 and ventricular lead 90. The combination of the leads 90 and 120 and the IPG 140 may constitute an implantable pacemaker of the type described in U.S. Pat. No. 5,312,446, hereby incorporated by reference.

Atrial lead 120 may be a unipolar or bipolar pacing lead, carrying one or two electrodes at atrial lead distal tip 130 located in the right atrial appendage of heart 100. The proximal end of atrial lead 120 is coupled to the input of an atrial sense amplifier 170 and the output of an atrial pace pulse generator 160. Similarly, ventricular lead 90 may be a unipolar or a bipolar lead, carrying one or two electrodes at ventricular distal tip 150 lodged in the right ventricular apex of heart 100. The proximal end of ventricular lead 90 is coupled to the input of an ventricular sense amplifier 190 and the output of an ventricular pace pulse generator 180.

The specific embodiment of the IPG 140 preferably operates in a DDD or DDDR pacing mode, wherein pacing pulses are delivered to both atrium and ventricle and wherein sensed atrial and ventricular depolarizations are both effective to inhibit delivery of the next scheduled pacing pulse in the chamber in which they are detected. The pacing rate may be adjusted between a lower and an upper pacing rate in response to an exercise related control signal developed from physiologic sensor 210 or in response to the intrinsic atrial rate in a manner well known in the art.

Within the housing of the IPG 140 are located the logic and timing circuit 200 which performs all of the basic timing, stimulation and sensing functions of a DDD or DDDR cardiac pacemaker, a microcomputer 240, which controls the timing intervals provided by the timing and logic circuitry 200, and associated components powered by a battery power source 110. Timing and logic circuitry 200 also includes a bi-directional telemetry circuit coupled to an IPG telemetry antenna 230, allowing transmission of information from external programmer 250 via programmer antenna 244 into the microcomputer 240 to modify operating modes and parameters. The bi-directional telemetry circuit within logic and timing circuit 200 also allows transmission of current operating and stored information from the IPG 140 to the external programmer 250 in a manner well known in the art.

In the practice of this embodiment of the invention, the atrial and ventricular leads 120 and 90 each include active LC resonant circuits of the unipolar or bipolar configurations of FIGS. 6 or 7, depending on the lead type. When it is desired to locate the lead tips, the patient is placed in the vicinity of the location system 20 and the X, Y and Z direction loops of antenna array 22. The programmer antenna 244 is placed over the IPG 140 and the programmer 250 is activated to program in a command to initiate the location mode for the selected atrial or ventricular lead 120 or 90, respectively. The logic and timing circuit 200 responds by activating the LC oscillator circuit 220 to generate an energizing pulse of the type shown in FIG. 2A and apply it to the appropriate lead conductor(s). The location system 20 then receives the radiated rF waveform and locates the lead tip in the manner described above. The second lead is then located in the same manner in response to the appropriate programmed in command.

During the delivery of the energizing pulse to a given lead 90 or 120, the sense amplifier coupled to that lead may be blanked to avoid any interference in a manner well known in the art. Pacing at a fixed rate may continue inasmuch as the high frequency, low amplitude pulse and pacing pulses do not interfere with one another in pacing the patient or in detection of the radiated rF signal.

This active LC resonant circuit approach may also be used in other types of stimulators, e.g., cardioverter/defibrillators, nerve or organ stimulators or the like having at least one lead conductor and an implanted source of power for the LC oscillator. In simpler monitors or pulse generators, other means may be provided for triggering the operation of LC oscillator 220 than the telemetry system described above. For example, the application of a magnetic field to close a reed switch or the like may be used to initiate the operation of the LC oscillator 220.

The system of the second embodiment may also be modified to be used in catheters having a conductor, e.g. a core wire or conductive shaft tube or coiled wire reinforcement that is insulated along its length by an outer sheath. In such a modification, it would be necessary to modify the location system 20 of FIG. 1 to directly apply the rF pulse to the proximal end of the conductor to cause the series LC circuit '10 to ring. The location of such a catheter would be effected in the same manner as described above with reference to FIG. 8.

It should also be noted that more than one LC resonant circuit 10 or '10 may be located along the length of the catheters or leads described above. In that case, the inductance and capacitance values for each LC resonant circuit 10 should be selected to ensure distinct resonant frequencies.

It should be further understood, of course, that the foregoing disclosure relates only to the best modes known to the inventor of the many possible modes of practicing the invention and that numerous modifications may be made various disclosed embodiments without departing from the spirit and scope of the invention as set forth in the appended claims.

PARTS LIST FOR FIGS. 1-8

LC resonant circuit 10
lead 12
implantable pulse generator (IPG) 14
lead tip 16
skin 18
location system 20
multiple loop antenna array 22
transceiver 24
transmitter oscillator and amplifier stage 26
receiver amplifier stage 28
radiated field 30
re-radiated field 32
signal processor 34
display 36
cylindrical capacitor plates 38, 40
inductor coil 42
conductor 44
tip electrode 46
side wall 48
hollow lumen catheter 50
distal tip end opening 52
bipolar lead 58
lead conductors 60, 62
tip electrode 64
ring electrode 66
unipolar lead 68
lead conductor 70
further electrode 72
ventricular lead 90
heart 100
battery power source 110
atrial lead 120
arterial distal tip 130
pace/sense IPG 140
connector block assembly 142
ventricular distal tip 150
atrial pace pulse generator 160
atrial sense amplifier 170
ventriculcar pace pulse generator 180
ventricular sense amplifier 190
logic and timing circuit 200
physiologic sensor 210
LC oscillator circuit 220
IPG telemetry antenna 230
microcomputer 240
programmer antenna 244
external programmer 250

I claim:

1. A method of locating a catheter in a patient's body comprising the steps of:
   providing a passive resonant circuit having a resonant oscillating frequency in a catheter distal tip region;
   generating a magnetic field outside the patient's body at the resonant oscillating frequency encompassing the patient's body and the implanted catheter for a predetermined time to induce a current in and cause the resonant circuit to store energy and oscillate;
   terminating the generated field, whereby the resonant circuit continues to oscillate as the stored energy is dissipated;
   detecting the continued oscillation of the resonant circuit; and
   determining the location of the catheter distal tip as a function of the re-radiated magnetic field produced by the continued oscillation of the resonant circuit.

2. The method of claim 1 wherein the passive resonant circuit is an LC tank circuit incorporated into the tip structure of the catheter.

3. The method of claim 1 wherein the passive resonant circuit is an LC tank circuit incorporated into the tip structure of a lead.

4. The method of claim 1 wherein the passive resonant circuit is an LC tank circuit incorporated into the tip structure of a pacing lead.

5. The method of claim 1 wherein:
   said detecting step further comprises sensing the intensity of the reradiated magnetic field in three orthogonal directions and providing signals representative thereof; and
   said determining step comprises determining the location of the catheter from said signals.

6. A system for locating a catheter in a patient's body, comprising:
   a catheter having a passive resonant circuit having a resonant oscillating frequency located therein;
   means for generating a field outside the patient's body at the resonant oscillating frequency encompassing the patient's body and the implanted catheter for a predetermined time interval to cause the resonant circuit to store energy and oscillate;
   means for detecting the continued oscillation of the resonant circuit at the expiration of the predetermined time interval; and
   means for determining the location of the catheter distal tip as a function of the magnetic field produced by the continued oscillation of the resonant circuit.

7. The system of claim 6 wherein the passive resonant circuit is an LC tank circuit incorporated into the tip structure of the catheter.

8. The system of claim 6 wherein the passive resonant circuit is an LC tank circuit incorporated into the tip structure of a lead.

9. The system of claim 6 wherein the passive resonant circuit is an LC tank circuit incorporated into the tip structure of a pacing lead.

10. The system of claim 6 wherein:
    said detecting means further comprises an antenna array for sensing the intensity of the re-radiated magnetic field in three orthogonal directions and providing signals representative thereof; and
    said determining means comprises means responsive to said signals for determining the location of the catheter.

* * * * *